(12) United States Patent
Laub et al.

(10) Patent No.: US 11,730,388 B2
(45) Date of Patent: Aug. 22, 2023

(54) MRI IMAGE RECONSTRUCTION USING MACHINE LEARNING (71) Applicant: Siemens Healthcare GmbH, Erlangen (DE)

(72) Inventors: Gerhard Laub, San Mateo, CA (US); Peter Schmitt, Weisendorf (DE); David Grodzki, Erlangen (DE); Waqas Majeed, Ellicott City, MD (US); Wuyi Zhao, Shenzhen (CN)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/897,571

(22) Filed: Jun. 10, 2020

(65) Prior Publication Data

US 2020/0405175 A1 Dec. 31, 2020

(30) Foreign Application Priority Data

Jun. 25, 2019 (CN) .......................... 201910554371.7

(51) Int. Cl.
*A61B 5/055* (2006.01)
*G01R 33/56* (2006.01)
*G01R 33/563* (2006.01)

(52) U.S. Cl.
CPC .......... *A61B 5/055* (2013.01); *G01R 33/5608* (2013.01); *G01R 33/5635* (2013.01)

(58) Field of Classification Search
CPC .......................... A61B 5/055; G01R 33/5608; G01R 33/5635; G16H 30/40; G16H 30/20
See application file for complete search history.

(56) References Cited

U.S. PATENT DOCUMENTS

| 10,614,597 B2 * | 4/2020 | Hoelzer ................ G06T 11/006 |
| 2017/0315200 A1 | 11/2017 | Kiefer et al. |
| 2020/0341094 A1 * | 10/2020 | Polak ................... A61B 5/7267 |

FOREIGN PATENT DOCUMENTS

JP 2015129987 A 7/2015

OTHER PUBLICATIONS

Rueda, Andrea, et. al., "Single-image super-resolution of brain MR images using overcomplete dictionaries", Medical Image Analysis 17.1, 2013, pp. 113-132.
S. Wang et al. "Accelerating Magnetic Resonance Imaging via Deep Learning", IEEE, 2016.
C. M. Hyun et al. "Deep learning for undersampled MRI reconstruction", Physics in Medicine & Biology, IPEM, 2018, vol. 63, Doi: https://doi.org/10.1088/1361-6560/aac71a.
Deep-Learning basierte Umrechnung von Bildern verschiedener Feldstärke, 2017.

(Continued)

*Primary Examiner* — Gregory H Curran
(74) *Attorney, Agent, or Firm* — Harness, Dickey & Pierce, P.L.C.

(57) ABSTRACT

In the field of MRI, a model-based MRI image reconstruction technique is provided. The model-based reconstruction technique increases the performance of Time-of-Flight MRA. In a learning phase, a model is calculated from a sufficiently large set of data acquired at both low and high magnetic fields, using deep learning strategies. In a clinical phase, the model is applied to measured data generating high MR image quality.

32 Claims, 3 Drawing Sheets (56) References Cited

OTHER PUBLICATIONS

O. Oktay et al. "Multi-Input Cardiac Image Super-Resolution using Convolutional Neural Networks", Biomedical Image Analysis Group, 2016.
C.-H. Pham et al. "Multi-scale brain MRI super-resolution using deep 3D convolutional networks", 2017.

* cited by examiner

MRI IMAGE RECONSTRUCTION USING MACHINE LEARNING

PRIORITY STATEMENT

This application claims priority under 35 U.S.C. § 119 to Chinese Patent Application number CN 201910554371.7 filed on Jun. 25, 2019, the contents of which are herein incorporated by reference in their entirety.

FIELD

Embodiments of the invention generally relate to MRI image reconstruction, specifically to Magnetic Resonance Angiography (MRA) image reconstruction, and more specifically to Time-of-Flight (TOF) MRA image reconstruction, using machine learning. Various examples particularly relate to TOF MRA image reconstruction using machine-learned (ML) algorithms.

BACKGROUND

Time-of-Flight (TOF) MR Angiography (MRA) is routinely used for clinical imaging of the intracranial vasculature, as e.g. it is non-invasive, does not need any kind of vascular contrast agents, and can be repeated many times in follow up studies. Not only the vessel lumen can be defined, it can also characterize the tissue in the vessel wall.

Typical TOF MRA techniques provide adequate image quality for typical B0 field strengths of 1.5 T and 3 T with acceptable SNR and scan times. To avoid increasing scan times, when using other magnetic B0 fields, various parameters may usually be changed.

According to traditional MR techniques, the spatial resolution may be changed, wherein the SNR scales linearly with the pixel, or voxel size, respectively. However, spatial resolution is very important for the imaging of the intracranial vasculature, and compromises need to be made between spatial resolution losses, and scan time increase.

Furthermore, the readout bandwidth may be changed, wherein the SNR scales inversely proportional to the square root of the bandwidth, i.e. a smaller bandwidth increases the SNR. However, a smaller bandwidth results in a longer readout time, which can be problematic when imaging moving objects such as blood in arteries or veins. Any kind of motion can result in localization errors, which is typically referred to as motion artifacts in MRI. Furthermore, the shorter T1 relaxation times at lower field strengths will result in a lower contrast between blood vessels and background signal tissue. This makes it more difficult to image smaller blood vessels.

Consequently, it is difficult to provide good image quality for MRI images, specifically TOF MRA images, without increasing the scan time and/or reducing the spatial resolution.

SUMMARY

Therefore, the inventors have discovered that using model-based MRI reconstruction techniques, to overcome or mitigate at least some the above-identified limitations and drawbacks, is a desirable approach.

Further advantageous features are subject matter of the claims.

At least one embodiment of the invention is described with respect to the claimed providing systems as well as with respect to the claimed methods. Features, advantages, or alternative embodiments herein may be assigned to the other claimed objects and vice versa. In other words, claims for the providing systems may be improved with features described or claimed in the context of the methods. In this case, the functional features of the method may be embodied by objective units of the providing system.

It is to be appreciated, that embodiments of the invention are described with respect to methods and systems for reconstructing a MRA image as well as with respect to methods and systems for providing trained functions for reconstructing an MRA image. Features, advantages, or alternative embodiments herein may be assigned to the other claimed objects and vice versa. In other words, claims for methods and systems for providing trained functions for reconstructing an MRA image may be improved with features described or claimed in context of the methods and systems for reconstructing a MRA image, and vice versa.

In particular, the trained functions, or in other words, trained machine learning functions or algorithms, of the methods and systems for reconstructing a MRA image may be adapted by features of the methods and systems for providing trained functions for reconstructing an MRA image. Furthermore, the MRA input images may comprise advantageous features and embodiments of the MRA input training data, and vice versa. Furthermore, the MRA output images may comprise advantageous features and embodiments of the MRA output data, and vice versa.

At least one embodiment is directed to a computer-implemented method for reconstructing a MRI image comprising:

receiving a first MRI image obtained at a first magnetic field strength including first imaging characteristics based on the first magnetic field strength;

generating a second MRI image including second imaging characteristics based on a second magnetic field strength, different from the first magnetic field strength, wherein the generating of the second MRI image includes applying trained functions to the first MRI image, the trained functions being trained with training MRI images obtained at the first magnetic field strength and reference MRI images obtained at the second magnetic field strength; and providing the second MRI image generated.

At least one embodiment is directed to a computing device configured for reconstructing an MRI image, the computing device comprising a memory, an interface and at least one processing unit, the memory containing instructions executable by the at least one processing unit, wherein execution of the instructions causes the computing device to execute at least:

receiving a first MRI image obtained at a first magnetic B0 field strength comprising first imaging characteristics based on the first magnetic B0 field strength;

generating a second MRI image comprising second imaging characteristics based on a second magnetic B0 field strength different from the first magnetic B0 field strength, wherein generating the second MRI image comprises applying trained functions to the first MRI image, which were trained with training MRI images obtained at the first magnetic B0 field strength and reference MRI images obtained at the second magnetic B0 field strength; and providing the second MRI image.

At least one embodiment is directed to a computing device configured for reconstructing an MRI image, the computing device comprising:

a memory;

an interface; and at least one processor, the memory containing instructions executable by the at least one processor, wherein execution of the instructions causes the computing device to execute at least:

receiving a first MRI image obtained at a first magnetic field strength including first imaging characteristics based on the first magnetic field strength;

generating a second MRI image including second imaging characteristics based on a second magnetic field strength, different from the first magnetic field strength, wherein the generating of the second MRI image includes applying trained functions to the first MRI image, the trained functions being trained with training MRI images obtained at the first magnetic field strength and reference MRI images obtained at the second magnetic field strength; and     providing the second MRI image generated.

At least one embodiment is directed to a computer-implemented method for providing trained functions for reconstructing a MRI image, comprising:

receiving training MRI images obtained at a first magnetic field strength including first imaging characteristics based on the first magnetic field strength;

receiving reference MRI images obtained at a second magnetic field strength, different from the first magnetic field strength, including imaging characteristics based on the second magnetic field strength;

generating processed MRI images for the training MRI images, wherein the generating of the processed MRI images includes applying functions to the training MRI images; and     determining a difference between the processed MRI images generated and reference MRI images;

training the functions based on the difference determined; and     providing the functions, trained in the training.

At least one embodiment is directed to an MRI system comprising at least one computing device of an embodiment.

At least one embodiment is directed to a computer program, comprising program code which is to be executed by at least one processor, wherein executing the program code causes the at least one processor to perform the method according to an embodiment.

At least one embodiment is directed to a computer-readable storage medium comprises instructions which, when executed by a computer, cause the computer to carry out one of the methods for reconstructing a MRA image or providing trained functions for reconstructing an MRA image according to an embodiment of the present disclosure.

At least one embodiment is directed to a non-transitory computer program product storing program code, executable by at least one processor, wherein executing of the program code causes the at least one processor to perform the method according to of an embodiment.

At least one embodiment is directed to a non-transitory computer-readable storage medium storing instructions which, when executed by a computer, cause the computer to carry out the method of an embodiment.

Although specific features described in the above summary and the following detailed description are described in connection with specific examples, it is to be understood that the features may not only be used in the respective combinations, but may also be used isolated, and features from different examples may be combined with each other, and correlate to each other, unless specifically noted otherwise.

Therefore, the above summary is merely intended to give a short overview over some features of some embodiments and implementations and is not to be construed as limiting. Other embodiments may comprise other features than the ones explained above.

BRIEF DESCRIPTION OF THE DRAWINGS

In the following, concepts in accordance with example embodiments of the invention will be explained in more detail with reference to the following drawings.

DETAILED DESCRIPTION OF EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment is directed to a computer-implemented method for reconstructing a MRI image. The method includes the following:

In a first step, a first MRI image is received. The first MRI image is obtained at a first magnetic B0 field strength. In general, obtaining an MRI image at a first magnetic B0 field may refer to acquiring the MRI image data using the first magnetic B0 field, or based on the first magnetic B0 field, which has a specific magnetic B0 field strength, wherein a MRI image is generated from the MRI measurement data.

In general, the first MRI image, the training MRI images, and the reference MRI images may be images of an examination object in an MRI system.

The first MRI image comprises first imaging characteristics based on the first magnetic B0 field strength. In general, imaging characteristics may be caused by a magnetic B0 field, specifically the field strength of the magnetic B0 field. For example, they may comprise one or more of a spatial resolution, a Signal-to-Noise Ratio (SNR), and a background/tissue contrast. In various examples, imaging characteristics may also refer to information contained in an MRI image.

In a next step, a second MRI image is generated, which comprises second imaging characteristics based on a second magnetic B0 field strength, which is different from the first magnetic B0 field strength. In other words, the second MRI image, which is generated by applying the trained functions to the first MRI image, may be a MRI image based on a second magnetic B0 field, or magnetic B0 field strength. Accordingly, a second MRI image may be generated, which has the same imaging characteristics, as a MRI image obtained at the second magnetic B0 field strength.

Generating the second MRI image comprises applying trained functions to the first MRI image, in other words generating the second MRI image may be effected by applying the trained functions to the first MRI image, whereby the second MRI image is generated. The trained functions are trained functions, which may be provided or received in a separate step.

According to various examples, the trained functions were trained with training MRI images, which were obtained at the first magnetic B0 field strength, and reference MRI images, which were obtained at the second magnetic B0 field strength.

In a further step, the second MRI image is provided.

A method for providing trained functions for reconstructing a MRI image is provided in the following as a separate method, which may be performed separately, and independently from the method for reconstructing an MRI image using the trained functions, wherein both methods may use the same first and second magnetic B0 fields.

A computer-implemented method for providing trained functions for reconstructing a MRI image comprises the following steps.

In a first step, training MRI images are received, wherein the training MRI images were obtained at a first magnetic B0 field strength. The training MRI images comprise first imaging characteristics based on the first magnetic B0 field strength.

In another step, reference MRI images are received. The reference MRI images are MRI images, which have been obtained in a measurement by a MRI system at a second magnetic B0 field strength different from the first magnetic B0 field strength. The reference MRI images comprise imaging characteristics based on the second magnetic B0 field strength.

In another step, processed MRI images are generated for the training MRI images. In various examples, for a training MRI image, a processed MRI image may be generated. For example for each training MRI image, a corresponding processed MRI image may be generated. Generating the processed MRI images comprises applying functions to the training MRI images. In various examples, the functions are applied to a training MRI image individually, to generate a corresponding processed MRI image.

In another step, a difference between the processed MRI images and the reference MRI images is determined. In various examples, determining a difference between the processed MRI images and the reference MRI images may comprise determining an individual difference between at least one, or each of the processed MRI images and a corresponding reference MRI image, and summing the individual differences, in order to determine the difference.

In another step, the functions are trained based on the determined difference.

In another step, the trained functions are provided.

By the techniques according to the invention, improved MRI images comparable may be provided, which have improved MRI image quality, such as more information, less distortions, higher tissue/background contrast, or a higher Signal-to-Noise ratio, and which further may be generated with shorter reconstruction time, compared to conventional techniques. In such a way, imaging tools may be offered e.g. at lower fields with similar image quality to a high field system, resulting in more reliable medical diagnoses in clinical applications.

A computing device is configured for reconstructing an MRI image by a method according to the present disclosure, the computing device comprising a memory, an interface, and at least one processing unit, the memory containing instructions executable by the at least one processing unit, wherein execution of the instructions causes the computing device to execute the following steps.

In a first step a first MRI image is received, which has been obtained at a first magnetic B0 field strength, comprising first imaging characteristics based on the first magnetic B0 field strength.

In a second step, a second MRI image is generated, comprising second imaging characteristics based on a second magnetic B0 field strength different from the first magnetic B0 field strength, wherein generating the second MRI image comprises applying trained functions to the first MRI image, which were trained with training MRI images obtained at the first magnetic B0 field strength and reference MRI images obtained at the second magnetic field strength.

In a further step, the second MRI image is provided.

The computing device may be further configured to perform any other method or any combination of methods according to the present disclosure.

A MRI system is configured or operative for performing any method for reconstructing a MRA image or providing trained functions for reconstructing an MRA image according to the present disclosure. A MRI system comprises at least one computing device according to the present disclosure.

A computer program product comprises program code to be executed by at least one processor of a computing device. Therein, the execution of the program code causes the at least one processor to execute one of the methods for reconstructing a MRA image or providing trained functions for reconstructing an MRA image according to the present disclosure.

A computer-readable storage medium comprises instructions which, when executed by a computer, cause the computer to carry out one of the methods for reconstructing a MRA image or providing trained functions for reconstructing an MRA image according to the present disclosure.

For such a computing device, MRI system, computer program product, and computer-readable storage medium for reconstructing a MRA image and for providing trained functions for reconstructing an MRA image, technical effects may be achieved, which correspond to the technical effects described for the methods for reconstructing a MRA image and for providing trained functions for reconstructing an MRA image.

The above and other elements, features, steps, and concepts of the present disclosure will be more apparent from the following detailed description in accordance with example embodiments of the invention, which will be explained with reference to the accompanying drawings.

Some examples of the present disclosure generally provide for a plurality of circuits, data storages, connections, or electrical devices such as e.g. processors. All references to these entities, other electrical devices, and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations, and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Time-of-Flight MR Angiography (TOF MRA) is used routinely for clinical imaging of the intracranial vasculature, due to its distinct advantages when compared to competing imaging modalities. MRI provides excellent soft tissue contrast, and is free from ionizing radiations. TOF MRA is non-invasive, it does not need any kind of vascular contrast agents, and can be repeated many times in follow up studies. Not only the vessel lumen can be defined, it can also characterize the tissue in the vessel wall.

Initially, TOF MRA was developed for the field strength of 1.5 T, and a scan time of a typical protocol is in the order of 5 to 8 minutes depending on coverage with adequate spatial resolution of 1 mm, or less. With the advent of 3 T systems the image quality took a boost mainly because of two effects. Firstly, the SNR increases approximately with the square root of the main magnet field B0, and secondly, the T1 times increase with B0. A longer T1 is beneficial in TOF MRA as it provides a better blood contrast (i.e. higher blood/background tissue ratio).

Typical TOF MRA techniques provide adequate image quality for typical B0 field strengths of 1.5 T and 3 T with acceptable SNR and scan times. To avoid increasing scan times at lower fields other parameters are usually changed.

According to traditional techniques, the spatial resolution may be changed, wherein the SNR scales linearly with the pixel, or voxel size, respectively. However, spatial resolution is very important for the imaging of the intracranial vasculature, and compromises need to be made between spatial resolution losses, and scan time increase.

Furthermore, the readout bandwidth may be changed, wherein the SNR scales inversely proportional to the square root of the bandwidth, i.e. a smaller bandwidth increases the SNR. However, a smaller bandwidth results in a longer readout time, which can be problematic when imaging moving objects such as blood in arteries or veins. Any kind of motion can result in localization errors, which is typically referred to as motion artifacts in MRI. Furthermore, shorter T1 relaxation will result in a lower contrast between blood vessels and background signal tissue. This makes it more difficult to image smaller blood vessels. Consequently, it is difficult to provide high-field image quality for TOF MRA with low magnetic B0 fields.

In general, Magnetic resonance angiography (MRA) is a group of techniques based on magnetic resonance imaging (MRI) to image blood vessels, wherein MRA is often used to evaluate the arteries of the heart and brain. A variety of techniques may be used to generate the pictures of blood vessels, both arteries and veins, based on flow effects, which are, therefore, referred to as flow-dependent or in other words inflow-based MRA methods, also called Time-of-Flight (TOF) MRA methods. They take advantage of the fact that the blood within vessels is flowing to distinguish the vessels from other static tissue.

In general, in the TOF method, blood flow that is not saturated, i.e. the inflow of unsaturated blood is utilized to generate stronger signals than MRI signals corresponding to the stationary tissue, which are in steady state within the volume and provide less signal compared to inflowing blood, for imaging blood vessels. Saturation may be effected by specific spatially variant or invariant saturation RF pulses. In inflow-based MR angiography, the sensitivity of the MRI signal to the movement of spins is used to generate images of vessels, especially arteries and occasionally veins. These are techniques, which exploit the influx of fresh unsaturated blood for hyperintense vascular imaging by transversal data acquisition with and without ECG triggering. Synonyms for such methods, which are based on unsaturated spins flowing into an imaging volume, are inflow-based MRI imaging techniques, time-of-flight (ToF) techniques, or single-flow techniques.

In general, flow dependent MRA may be divided into different categories. There is phase-contrast MRA (PC-MRA) which utilizes phase differences to distinguish blood from static tissue and time-of-flight MRA (TOF MRA), which exploits the signal difference between unsaturated, inflowing blood and saturated, stationary tissue in the imaging volume.

In general, time-of-flight (TOF) methods may be based on a T1 contrast, in other words may be T1-weighted, using short echo time and flow compensation to make flowing blood much brighter than stationary tissue. As flowing blood enters the area being imaged, the inflowing blood ideally hasn't seen any excitation pulses. As it travels through the imaging volume it will experience excitation pulses and get progressively saturated, thus providing higher signal than the saturated stationary tissue. As this method is dependent on flowing blood, areas with slow flow (such as large aneurysms) or flow that is in plane of the image may not be well visualized. TOF MRA is commonly used in the head and neck, and provides for detailed high-resolution images. It is also the most common technique used for routine angiographic evaluation of the intracranial circulation in patients with ischemic stroke.

In general, a trained function mimics cognitive functions that humans associate with other human minds. In particular, by training based on training data the trained function is able to adapt to new circumstances and to detect and extrapolate patterns.

In general, parameters of a trained function may be adapted by means of training. For example, supervised training, semi-supervised training, unsupervised training, reinforcement learning and/or active learning may be used. Furthermore, representation learning (an alternative term is "feature learning") may be used. In particular, the parameters of the trained functions may be adapted iteratively by several steps of training.

In general, a trained function may comprise a neural network, a support vector machine, a decision tree and/or a Bayesian network, and/or the trained function may be based on k-means clustering, Q-learning, genetic algorithms and/or association rules. In particular, a neural network may be a deep neural network, a convolutional neural network or a convolutional deep neural network. Furthermore, a neural network may be an adversarial network, a deep adversarial network and/or a generative adversarial network.

In general, the step of applying trained functions to the MRA images may be performed by a variational network, wherein a variational network may comprise a neural network, and/or a Convolutional Neural Network (CNN), and/or a forward sampling operator.

In general, a CNN network may comprise a plurality of trained filter functions, using trained filter parameters, wherein, in each of a plurality of steps each trained filter function in the neural network may be applied to a sub-volume of the MRI images simultaneously, using convolutions and non-linear activations, to provide an output of the neural network.

In general, in the method for reconstructing a MRI image by a the neural network, only MRI images may be used as an input, wherein MRI measurement data, and/or coil sensitivities, and/or parameters of MRI protocols may not be used and/or may not be an input to the neural network.

MRI techniques are known from the documents Rueda, Andrea, Norberto Malpica, and Eduardo Romero. "Single-image super-resolution of brain MR images using overcomplete dictionaries." Medical image analysis 17.1 (2013): 113-132; JP 2015-129987 A; Oktay, Ozan, et al. "Multi-input cardiac image super-resolution using convolutional neural networks." International conference on medical image computing and computer-assisted intervention. Springer, Cham, 2016; Wang, Shanshan, et al. "Accelerating magnetic resonance imaging via deep learning." 2016 IEEE 13th International Symposium on Biomedical Imaging (ISBI). IEEE, 2016; Hyun, Chang Min, et al. "Deep learning for undersampled MRI reconstruction." Physics in Medicine & Biology 63.13 (2018): 135007; Pham, Chi-Hieu, Ronan Fablet, and Francois Rousseau. "Multi-scale brain MRI super-resolution using deep 3D convolutional networks." (2017); and US 2017/0315200 A1. The entire contents of each of the aforementioned documents are hereby incorporated herein by reference.

Figure 1:
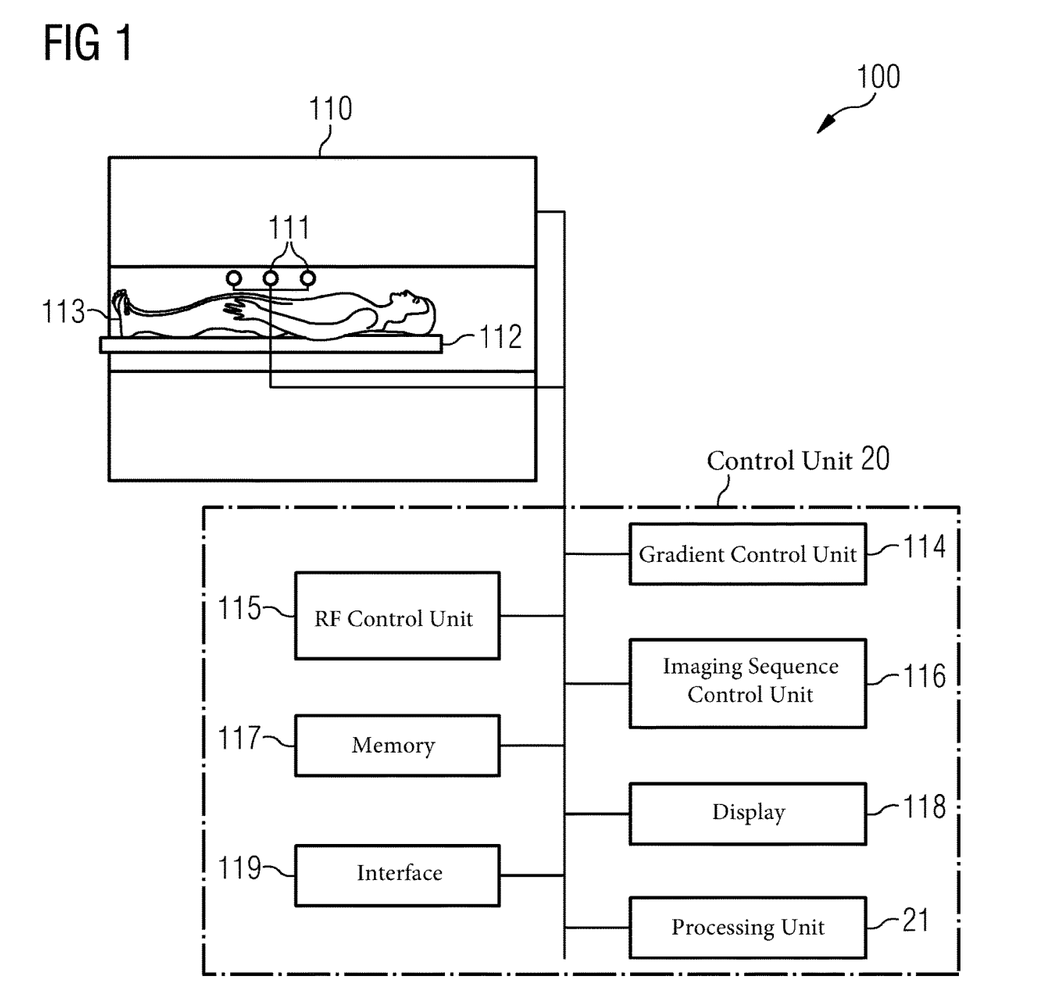
FIG. 1 schematically illustrates a MRI system, according to embodiments of the invention.

FIG. 1 schematically illustrates a MRI system 100, according to embodiments of the invention.

As depicted in FIG. 1, the MRI system 100 comprises a magnet 110, generating a polarization field B0.

In general, the magnet 110 provides a DC magnetic field, which may be referred to as magnetic B0 field B0, B0 field, or basic and/or polarization field B0, and which may have a low field strength near 0 or a high strength of up to 20 Tesla (T) or more along its longitudinal axis. For example, some clinical magnets generally may have a field strength in the range 0.1-3.0 T, with research systems available up to 9.4 T for human use, or 21 T for animal systems, wherein it is to be noted, that the techniques according to the present disclosure are applicable to any magnetic field strength, and are in no way limited to a certain magnetic field strength. The main static magnetic field aligns the magnetization of spins of an object to be examined along the direction of the B0 field, i.e. along its longitudinal axis.

For many MRI applications, homogeneity of the magnetic B0 field in an examination volume from which MRI measurement signals are acquired, is crucial for MRI image quality and for spatial registration of MRI images with regard to MRI image distortions. In order to suppress B0 inhomogeneity, shim coils, which can be part of a gradient coil, or local shim coils, which can be extra coils or part of local coils, are commonly used. In order to obtain optimal results, the current through the shim coils is optimized so that the B0 field becomes as homogeneous as possible in the measurement volume.

The magnetic B0 field strength, described in Tesla, of the B0 field in the homogeneity volume may be referred to as the strength of the magnetic B0 field, or B0 field strength. Accordingly, the magnetic B0 field strength may correspond to a maximum magnetic field strength of the B0 field applied in an MRI system, in particular in the examination volume of the MRI system. Accordingly, the B0 field strength B0 may correspond to the nominal magnetic field strength of the B0 field, wherein the real values of the B0 field at each location may slightly deviate within specification limits of the MRI system, as known in the art. Accordingly, the average magnetic field strength of the B0 field in the examination volume MRI system may be referred to as B0 magnetic field strength.

An object under examination 113 lying on a table 112 is moved into the center of the MRI system 9, where MRI signals after RF excitation can be detected by receiving coils 111 which can comprise different coil sections, wherein each coil section can be associated with a corresponding detection channel. By applying RF pulses and magnetic field gradients, the nuclear spins in the object 113, especially the part located in the receiving coil, are excited and location-coded and the currents induced by the relaxation can be detected. The way how MRI images are generated and how MRI signals are detected using a sequence of RF pulses and the sequence of magnetic field gradients is known in the art, and is discussed herein with regard to the other figures, so that a detailed explanation thereof is omitted.

The MRI system 100 comprises a control unit 20, which is used for controlling the MRI system. The control unit 20 comprises a gradient control unit 114 for controlling and switching the magnetic field gradients, and an RF control unit 115 for controlling and generating the RF pulses for the imaging sequence. An imaging sequence control unit 116 is provided which controls the sequence of the applied RF pulses and magnetic field gradients and thus controls the gradient control unit, the RF control unit, and the receiving coils 111. In a memory 117, computer programs needed for operating the MRI system and the imaging sequences necessary for generating the MRI images can be stored together with the generated MRI images. The generated MRI images can be displayed on a display 118, wherein an input unit or human-machine interface 119 is provided used by a user of the MRI system to control the functioning of the MRI system. A processing unit 21 comprising one or more processors which can carry out instructions stored on the memory 117. The memory can furthermore include a suitable program code to be executed by the processing unit 21. The processing unit can, based on the detected images, reconstruct an MRI image.

As will be discussed below, the control unit 20 and/or the processing unit 21 can be configured such that a method for reconstructing a MRI image and a method for providing trained functions for reconstructing a MRI image according to the present disclosure can be carried out.

Detailed descriptions of MRI image reconstruction, providing trained functions for MRI image reconstruction, and ML and/or DL reconstruction techniques in accordance with aspects and embodiments of the invention will be explained.

Figure 2:
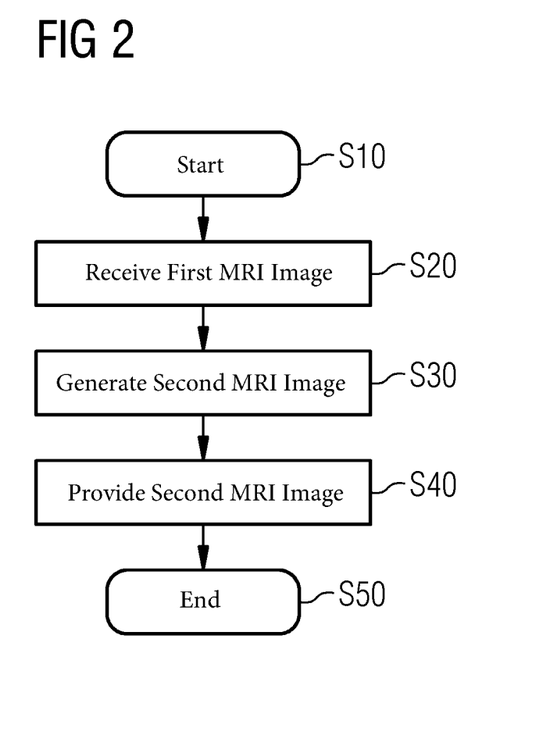
FIG. 2 illustrates a flow chart of a method for reconstructing a MRI image, according to embodiments of the invention.

FIG. 2 illustrates a flow chart of a method for reconstructing a MRI image, according to embodiments of the invention.

The methods according to the present disclosure uses deep learning and a model-based reconstruction to calculate high-quality MRI images, specifically TOF MRA images, from a data set which was measured e.g. at a lower field strength. The methods may have several phases, which will be described in the following.

The computer-implemented method for reconstructing a MRI image starts in step S10.

In step S20, a first MRI image is received. In general, receiving data, such as MRI images or functions, may comprise receiving stored data from internal or external memory or data storage, and/or transmitting the data from a MRI measurement system or a computing device, were they may have been measured, and/or computed, and/or stored, wherein any known method of transmitting or receiving data may be implemented.

The first MRI image is obtained at a first magnetic B0 field strength. In general, obtaining an MRI image at a magnetic B0 field may refer to obtaining, or acquiring, an MRI image at the magnetic B0 field, or based on the magnetic B0 field having a magnetic B0 field strength, wherein MRI measurement data of the MRI image is acquired applying the magnetic B0 field strength to the examination region or the examination object in the examination region, and/or based on the magnetic B0 field strength.

In various embodiments, the first MRI image may be at least one first MRI image, or maybe a plurality of first MRI images, to be further processed together in order to provide at least one second MRI image. For example, the plurality of first MRI images may be processed simultaneously in a convolutional neural network, in order to provide the at least one second MRI image.

In general, the first MRI image, the training MRI images, and the reference MRI images may be images of an examination object in an MRI system. Specifically, these MRI images may be images of the same examination object, and/or acquired using the same MRI system, wherein for example training MRI images and corresponding reference MRI images may be acquired using the same examination region, and/or the same field of view, and/or the same measurement angle, of the examination object in the MRI system. However, it is to be understood, that in some examples different MRI systems may be used, and/or different examination objects may be used for training the functions.

The first MRI image comprises first imaging characteristics based on the first magnetic B0 field strength. In general, imaging characteristics may refer to features, properties, details and/or attributes of an MR image, or of MR measurement data, which contribute to the MR image quality, wherein the imaging characteristics may be typical for, or based on a magnetic B0 field, or a magnetic B0 field strength. The imaging characteristics may be typical and/or caused the magnetic B0 field strength, and/or may comprise typical measurement information or imaging details for the specific B0 field strength. For example, they may comprise a spatial resolution, and/or a Signal-to-Noise Ratio (SNR), and/or a background/tissue contrast. In various examples, imaging characteristics may also refer to information contained in the MRI images. The MRI imaging characteristics may be based, correspond to, or be effected/caused by application or using the specific magnetic B0 field, or the specific magnetic B0 field strength. As such, they may refer to maximum values obtainable at the specific magnetic B0 field strength.

In step S30, a second MRI image is generated, which comprises second imaging characteristics based on a second magnetic B0 field strength different from the first magnetic B0 field strength. The second MRI image, which is generated by applying the trained functions to the first MRI image, may be a MRI image based on a second magnetic B0 field, or magnetic B0 field strength. In other words, the second MRI image may be generated having the same characteristics, or imaging characteristics, as a MRI image acquired, or obtained, at the second magnetic B0 field strength.

Generating the second MRI image comprises applying trained functions to the first MRI image, in other words generating may be effected by applying the trained functions to the first MRI image, whereby a second MRI image is generated. The trained functions are trained functions, which may be provided or received.

As a general rule, the first magnetic B0 field strength may be lower at the second magnetic B0 field strength. However, in various other examples, the second magnetic B0 field strength may lower than the first magnetic B0 field strength. In various examples, the second magnetic B0 field strength may be lower or higher than the first magnetic B0 field strength.

The trained functions were trained with training MRI images, which were obtained at the first magnetic B0 field strength, and reference MRI images, which were obtained at the second magnetic B0 field strength.

In general, the trained functions may have been trained with training data, in other words using, or based on, training data, the training data not including the first MRI image, before performing the method for reconstructing a MRI image, in a method for providing trained functions for reconstructing a MRI image.

In step S40, the second MRI image is provided. The method ends in step S50.

Figure 3:
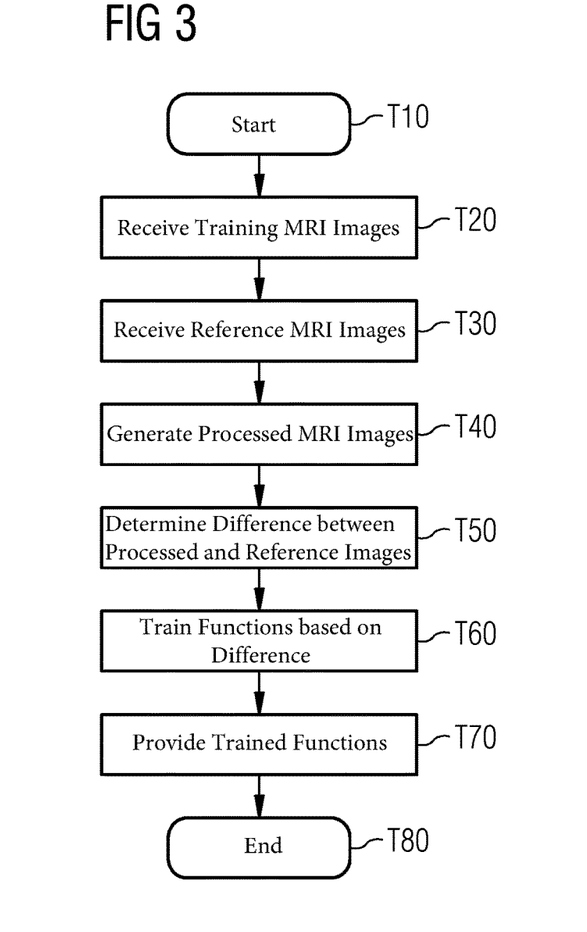
FIG. 3 illustrates a flow chart of a method for providing trained functions for reconstructing an MRI image, according to embodiments of the invention.

FIG. 3 illustrates a flow chart of a method for providing trained functions for reconstructing an MRI image, according to embodiments of the invention.

The computer-implemented method for providing trained functions for reconstructing a MRI image starts in step T10.

Steps T20 and T30 relate to an input phase, in which a sufficiently large data set of TOF MRA is acquired at low and at high field from an examination object, specifically in volunteers and/or patients. The volunteer/patient data, or all volunteer/patient data, may be acquired at the same field strengths (e.g. 0.2 T and 7 T) with fixed protocols for each of the field strength.

In step T20, training MRI images are received, wherein the training MRI images where obtained at a first magnetic B0 field strength, and may e.g. also be referred to as low-field data set. The low-field data set may, for example, be acquired with a lower spatial resolution, and lower vessel to background tissue contrast in approximately the same scan time (or slightly longer) at a field strength of 0.2 T, as an example. The training MRI images comprise first imaging characteristics based on the first magnetic B0 field strength.

In step T30, reference MRI images are received. The reference MRI images are MRI images, which have been obtained at a second magnetic B0 field strength different from the first magnetic B0 field strength. In examples, where the second magnetic B0 field is higher than the first B0 field, it may also be referred to as high-field data set. The high-field data set may, for example, be acquired with a typical clinical protocol (preferably at 3 T) with high spatial resolution. The reference MRI images comprise imaging characteristics based on the second magnetic B0 field strength.

Steps T40, T50, and T60 refer to a learning phase, or in other words a training phase of the trained functions.

Therein, a geometric alignment of the low-field and high-field data set may be performed via landmarks, such as an anatomical structure or a plurality of anatomical structures, in the images of the same volunteer/patient acquired at high and low field. For example, the circle of willis may be used as anatomical structure for this purpose.

In step T40, processed MRI images are generated for the training MRI images. Generating the processed MRI images comprises applying functions to the training MRI images.

Each data set may be divided into multiple sub-volumes of M×M×M at low field and N×N×N at high field. N and M are chosen such that the physical size of each sub-volume is the same. A deep learning algorithm determines the model which optimally transforms the low-field subvoxel into the high-field subvoxel. For each training MRI image, a corresponding processed MRI image may be generated.

Furthermore, the learning phase may comprise an annotation of the training data and feeding annotations into the deep-learning procedure. Especially, the annotation of a) clinical findings in the data set(s) and b) field strength specific differences between the two data sets can be fed into the training algorithm, so that the model is able to reconstruct those in the low field data set. As an automated training approach, the subtraction image of the high- and low field data set can be used in order to annotate the differences between the image content of the high- and low field acquisitions.

In step T50, a difference between the processed MRI images and the reference MRI images is determined. In various examples, determining a difference between the processed MRI images and the reference MRI images may comprise determining an individual difference for each of the processed MRI images and a corresponding reference MRI image, and summing the individual differences, in order to determine the difference.

In step T60, the functions are trained based on the determined difference.

Training the functions may be performed in iterative algorithm, wherein the steps of generating processed MRI images, and determining a difference between the processed MRI images and the reference MRI images, is iterated, using the trained functions of a previous iteration for the next iteration, thus improving the trained functions and an iterative way.

In step T70, the trained functions are provided. The method ends in step T80.

Referring back to FIG. 2, in an application phase using the method for reconstructing an MRI image based on the trained functions, the model, which was determined in the learning phase, is applied to the data set, which was acquired at low field. During the reconstruction, the missing information or low SNR within the low field acquisitions may be reconstructed based on the learned model.

Figure 4:
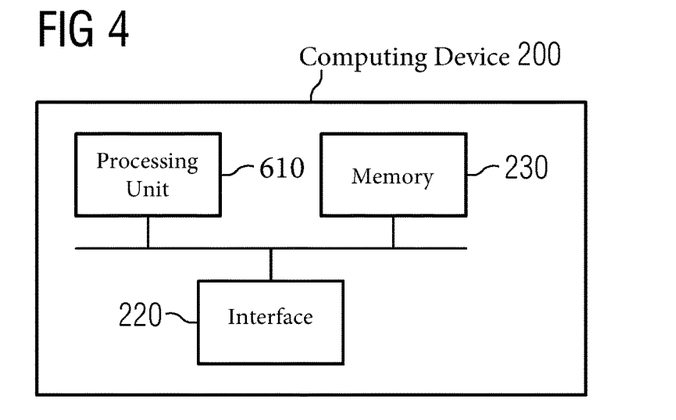
FIG. 4 illustrates a schematic drawing of a device according to embodiments of the invention.

FIG. 4 illustrates a schematic drawing of a device 200 according to embodiments of the invention.

The device, or computing device, 200 is configured for reconstructing an MRI image and/or for providing trained functions for reconstructing an MRI image, wherein the computing device 200 comprises a memory 230, an interface 220, and at least one processing unit 610. Therein, the memory 230 contains instructions executable by the at least one processing unit 610, wherein execution of the instructions causes the computing device 200 to execute the steps as described for FIG. 2 and FIG. 3.

From the above the, some general conclusions may be drawn:

The first magnetic field strength may be in the range of 0.1-1 T, specifically in the range of 0.1-0.7 T, and more specifically in the range of 0.35-0.6 T.

The second magnetic field strength may be in the range of 1-7 T, specifically in the range of 1.5-3 T, and more specifically is 3 T.

These ranges provide for specifically efficient MRI image reconstruction by trained functions in clinical applications.

The method for providing trained functions may be improved with at least one of the following features. Accordingly, the method for reconstructing an MRI image may be improved, wherein the trained functions were trained comprising at least one of the following features.

Training the functions with training MRI images and reference MRI images may comprise performing a geometric alignment of the training MRI images and the reference MRI images using landmarks in the MRI images, specifically using at least one anatomical structure.

Applying functions to the training MRI images and reference MRI images may comprise the following steps.

In a first step, the training MRI images may be divided into multiple first sub-volumes, in particular M×M×M first sub-volumes.

In another step, the reference MRI images may be divided into multiple second sub-volumes, in particular N×N×N second sub-volumes, wherein the physical size of the first and second sub-volumes may be the same. Specifically, a physical size of a sub-volume of the first sub-volumes may be the same as the physical size of a corresponding sub-volume of the second sub-volumes.

In another step, the functions may be applied to the first sub-volumes.

Training the functions with training MRI images and reference MRI images may comprise determining a model, which transforms the first sub-volumes into the second sub-volumes, specifically each of the first sub-volumes into a corresponding second sub-volume.

Training the functions with training MRI images and reference MRI images may comprise annotating the training and/or reference MRI image with clinical findings in at least one of the MRI images, and/or with B0 field strength specific differences between the image contents of the MRI images.

Annotating of B0 field strength specific differences may comprise annotating one or more of the imaging characteristics.

Annotating B0 field strength specific differences between the MRI images may comprise using subtraction images of the training images and the corresponding reference images, specifically a subtraction image between a training MRI image and the corresponding reference MRI image.

The MRI images may be Time-of-Flight (TOF) Magnetic Resonance Angiography (MRA) images, wherein MRI measurement data is acquired using a Time-of-Flight (TOF) Magnetic Resonance Angiography (MRA) measurement technique.

Trained functions may be applied to the first MRI image by a neural network, in particular using a model-based deep-learning mechanism. Accordingly, the trained functions may be trained using a neural network, in particular using a model-based deep-learning mechanism.

The first imaging characteristics may be different from the second imaging characteristics, and/or the first MRI image may not comprise the second imaging characteristics, and/or the second MRI image may not comprise the first imaging characteristics.

The first imaging characteristics may comprise a first spatial resolution, wherein the second imaging characteristics may comprise a second spatial resolution, and/or wherein the first spatial resolution may be lower than the second spatial resolution.

The first imaging characteristics may comprise a first blood/background tissue contrast, wherein the second imaging characteristics may comprise a second blood/background tissue contrast, and/or wherein the first blood/background tissue contrast may be lower than the second blood/background tissue contrast.

The first image may be acquired with a first Signal-to-Noise Ratio (SNR), i.e. SNR of the underlying MRI measurement data and/or MRI measurement signal, wherein the reference MRI images may be acquired with a second SNR, and/or wherein the first SNR may be lower than the second SNR.

The first and the second MRI images may be acquired with the same MRI measurement time, and/or the same MRI measurement bandwidth, and/or the same MRI contrast, and/or the same spatial resolution.

By the general conclusions, training the functions, and applying the trained functions to a MRI image may be greatly improved by providing higher accuracy of MRI image reconstruction, in particular of the accuracy and speed of the machine-learned functions.

It is to be appreciated, that the techniques according to the present disclosure may also be applied to the underlying MRI measurement data accordingly, instead of to MRI images, wherein similar effects may be reached.

In various examples, the training MRI images and reference MRI images may be acquired using a fixed MRI measurement protocol for each magnetic B0 field strength.

Summarizing, in the field of MRA, a model-based MRA image reconstruction technique is provided, wherein the model-based reconstruction technique according to the present disclosure overcomes the limitations of low-field Time-of-Flight MRA, and provides high-field image quality. In a learning phase, a machine-learning model is calculated from a training data set, which is acquired at both low and high magnetic B0 field strength, using deep learning strategies. In a clinical phase, the model is applied to low-field MR images, in order to generate MR images with high-field image quality.

Thereby, the improved method according to the present disclosure provides improved MRI image quality at a low B0 field strength, specifically by using deep learning and a model-based reconstruction to calculate high-quality TOF MRA images from a data set, which was measured at a lower field strength with lower spatial resolution, resulting in more reliable medical diagnoses in clinical applications.

Although the invention has been shown and described with respect to certain preferred embodiments, equivalents and modifications will occur to others skilled in the art upon the reading and understanding of the specification. The present invention includes all such equivalents and modifications and is limited only by the scope of the appended claims.

It will be appreciated, that similar techniques may be applied to other MRI contrasts and other combinations of imaging modalities, e.g. low field MR and CT, or PET and high-field MRI. Furthermore, the proposed approach can be used to increase the quality of TOF images acquired on 1.5 T to 3 T or higher.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for reconstructing a MRI image, comprising:
    acquiring first MRI measurement data at a first magnetic field strength using an MRI system;
    generating a first MRI image based on the first MRI measurement data, the first MRI image having first imaging characteristics based on the first magnetic field strength;
    generating a second MRI image by applying trained functions to the first MRI image, the second MRI image having second imaging characteristics, the second imaging characteristics corresponding to a second magnetic field strength different from the first magnetic field strength, the trained functions having been trained using training MRI images and reference MRI images, the training MRI images being obtained at the first magnetic field strength, and the reference MRI images being obtained at the second magnetic field strength; and
    providing the second MRI image.

2. The method of claim 1, wherein the first imaging characteristics and the second imaging characteristics include one or more of a Signal-to-Noise-Ratio (SNR), a spatial resolution, a tissue/background contrast, and a readout bandwidth.

3. The method of claim 2, wherein the trained functions have been trained by:
    receiving training MRI images obtained at a third magnetic field strength, the training MRI images having first imaging characteristics based on the third magnetic field strength;
    receiving reference MRI images obtained at a fourth magnetic field strength different from the first third magnetic field strength, the reference MRI images having imaging characteristics based on the fourth magnetic field strength;
    generating processed MRI images including applying functions to the training MRI images;
    determining a difference between the processed MRI images and reference MRI images;
    training the functions based on the difference to obtain the trained functions; and
    providing the trained functions.

4. The method of claim 2, wherein the first MRI image and the second MRI image are Time-of-Flight (TOF) Magnetic Resonance Angiography (MRA) images.

5. The method of claim 2, wherein the second magnetic field strength is higher than the first magnetic field strength.

6. The method of claim 1, wherein the trained functions have been trained by:
    receiving training MRI images obtained at a third magnetic field strength, the training MRI images having first imaging characteristics based on the third magnetic field strength;
    receiving reference MRI images obtained at a fourth magnetic field strength different from the third magnetic field strength, the reference MRI image having imaging characteristics based on the fourth magnetic field strength;
    generating processed MRI images including applying functions to the training MRI images;
    determining a difference between the processed MRI images and the reference MRI images;
    training the functions based on the difference to obtain the trained functions; and
    providing the trained functions.

7. The method of claim 1, wherein the first MRI image and the second MRI image are Time-of-Flight (TOF) Magnetic Resonance Angiography (MRA) images.

8. The method of claim 1, wherein the trained functions have been trained using a neural network.

9. The method of claim 1, wherein the second magnetic field strength is higher than the first magnetic field strength.

10. A computing device for reconstructing an MRI image, the computing device being configured to perform the method of claim 1.

11. An MRI system, comprising at least one computing device of claim 10.

12. A non-transitory computer program product storing program code that, when executed by at least one processor, causes the at least one processor to perform the method according to claim 1.

13. A non-transitory computer-readable storage medium storing instructions which, when executed by a computer, cause the computer to carry out the method of claim 1.

14. The method of claim 1, wherein the trained functions have been trained using a neural network that provides a model-based deep-learning mechanism.

15. The method of claim 1, wherein the acquiring comprises acquiring the first MRI measurement data from at least one receiving coil of the MRI system based on at least one radio frequency pulse.

16. The method of claim 15, wherein the generating the first MRI image comprises reconstructing the first MRI image based on the first MRI measurement data.

17. The method of claim 15, wherein the acquiring comprises acquiring the first MRI measurement data based on MRI signals received from an object under examination in response to the at least one radio frequency pulse being applied to the object under examination at the first magnetic field strength.

18. A computer-implemented method for providing trained functions for reconstructing a MRI image, comprising:
acquiring first MRI measurement data and second MRI measurement data using an MRI system, the first MRI measurement data being obtained at a first magnetic field strength, and the second MRI measurement data being obtained at a second magnetic field strength different from the first magnetic field strength;
generating training MRI images based on the first MRI measurement data, the training MRI images having first imaging characteristics based on the first magnetic field strength;
generating reference MRI images based on the second MRI measurement data, the reference MRI images having imaging characteristics based on the second magnetic field strength;
generating processed MRI images including applying functions to the training MRI images;
determining a difference between the processed MRI images and the reference MRI images;
training the functions based on the difference to obtain trained functions; and
providing the trained functions.

19. The method of claim 18, further comprising:
performing a geometric alignment of the training MRI images and the reference MRI images using landmarks in the training MRI images and the reference MRI images.

20. The method of claim 19, wherein the performing the geometric alignment performs the geometric alignment using at least one anatomical structure.

21. The method of claim 19, wherein the generating the processed MRI images comprises:
dividing the training MRI images into multiple first sub-volumes;
dividing the reference MRI images into multiple second sub-volumes, the first sub-volumes being a same physical size as the second sub-volumes; and
applying the functions to the first sub-volumes.

22. The method of claim 19, further comprising:
annotating at least one of the training MRI images or the reference MRI images with at least one of,
a clinical finding, or
a field strength specific difference between a respective training MRI image among the training MRI images and a respective reference MRI image among the reference MRI images.

23. The method of claim 18, wherein the generating the processed MRI images comprises:
dividing the training MRI images into multiple first sub-volumes;
dividing the reference MRI images into multiple second sub-volumes, the first sub-volumes being a same physical size as the second sub-volumes; and
applying the functions to the first sub-volumes.

24. The method of claim 23, further comprising:
annotating at least one of the training MRI images or the reference MRI images with at least one of,
a clinical finding, or
a field strength specific difference between a respective training MRI image among the training MRI images and a respective reference MRI image among the reference MRI images.

25. The method of claim 18, further comprising:
annotating at least one of the training MRI images or the reference MRI images with at least one of,
a clinical finding, or
a field strength specific difference between a respective training MRI image among the training MRI images and a respective reference MRI image among the reference MRI images.

26. The method of claim 18, wherein the training MRI images and the reference MRI images are Time-of-Flight (TOF) Magnetic Resonance Angiography (MRA) images.

27. The method of claim 18, wherein the method is performed using a neural network.

28. The method of claim 18, wherein the trained functions have been trained using a neural network that provides a model-based deep-learning mechanism.

29. A non-transitory computer program product storing program code that, when executed by at least one processor, causes the at least one processor to perform the method according to claim 18.

30. A non-transitory computer-readable storage medium storing instructions which, when executed by a computer, cause the computer to carry out the method of claim 18.

31. A computing device configured for reconstructing an MRI image, the computing device comprising:
a memory containing instructions;
an interface; and
at least one processor configured to execute the instructions to cause the computing device to,
acquire first MRI measurement data at a first magnetic field strength using an MRI system,
generate a first MRI image based on the first MRI measurement data, the first MRI image having first imaging characteristics based on the first magnetic field strength,
generate a second MRI image by applying trained functions to the first MRI image, the second MRI image having second imaging characteristics, the second imaging characteristics corresponding to a second magnetic field strength different from the first magnetic field strength, the trained functions having been trained with training MRI images and reference MRI images, the training MRI images being obtained at the first magnetic field strength, and the reference MRI images being obtained at the second magnetic field strength, and
provide the second MRI image.

32. An MRI system, comprising at least one computing device of claim 31.

* * * * *